(12) United States Patent
Amaral et al.

(10) Patent No.: US 7,358,267 B2
(45) Date of Patent: Apr. 15, 2008

(54) BIS-ARYL THIAZOLE DERIVATIVES

(75) Inventors: M. Catherine Amaral, Roswell, GA (US); Jin-Long Chen, San Mateo, CA (US); Juan C. Jaen, Burlingame, CA (US); David N. Johnston, Didcot (GB); Paul Rafferty, Westbourough, MA (US)

(73) Assignee: Amgen Inc., Thousand Oaks, CA (US)

( * ) Notice: Subject to any disclaimer, the term of this patent is extended or adjusted under 35 U.S.C. 154(b) by 471 days.

(21) Appl. No.: 10/481,218

(22) PCT Filed: Jun. 27, 2002

(86) PCT No.: PCT/US02/20447

§ 371 (c)(1),
(2), (4) Date: Jul. 12, 2004

(87) PCT Pub. No.: WO03/002062

PCT Pub. Date: Jan. 9, 2003

(65) Prior Publication Data

US 2005/0215608 A1  Sep. 29, 2005

Related U.S. Application Data

(60) Provisional application No. 60/302,193, filed on Jun. 29, 2001.

(51) Int. Cl.
- *A61K 31/427* (2006.01)
- *A61K 31/428* (2006.01)
- *C07D 277/50* (2006.01)
- *C07D 277/82* (2006.01)

(52) U.S. Cl. ..................... 514/370; 548/194
(58) Field of Classification Search ............. 548/194; 514/370
See application file for complete search history.

(56) References Cited

U.S. PATENT DOCUMENTS

| | | | |
|---|---|---|---|
| 5,342,851 A | 8/1994 | Sanfilippo et al. | 514/370 |
| 5,849,581 A | 12/1998 | Hirose et al. | 123/357 |
| 6,492,401 B1 * | 12/2002 | Hamanaka et al. | 514/359 |

FOREIGN PATENT DOCUMENTS

WO   WO 96/05861   2/1996

OTHER PUBLICATIONS

Sanfilippo et al., "Novel Thiazole-Based Heterocycles as Selective Inhibitors of Fibrinogen-Mediated Platelet Aggregation," J. Med. Chem., vol. 38, pp. 34-41 (1995).*
Kapoor et al. Indian Journal of Heterocyclic Chemistry 1997, 7(1), 1-4.*
Crowe et al. Breast Cancer Research 2004, 6(5), R546-R555.*
Gunter et al. Journal of Nutritional Biochemistry 2006, 17, 145-156.*
Harper et al. Current Opinions in Pharmacology 2004, 4, 603-7.*
Argyropoulos, George, et al., "Effects of Mutations in the Human uncoupling Protein 3 Gene on the Respiratory Quotient and Fat Oxidation in Severe Obesity and Type 2 Diabetes", J. Clin. Invest., 102:(7), Oct. 1998, 1345-1351.
Boss, Oliver, et al., "Uncoupling protein-3: a new member of the mitochondrial carrier family with tissue- specific expression", FEBS Lett., 1997, 408 :39-42.
Boss, Oliver, et al., "Genomic Structuring of Uncoupling Potein-3 (UCP3) and Its Assignment to Chromosome 11q13", Genomics, 1998, 47:425-426.
Bouchard, Claude, et al., "Linkage between markers in the vicinity of the uncoupling protein 2 gene and resting metabolic rate in humans", Hum. Molec. Genet., 1997, 6 (11):1887-1889.
Brown Angela, et al., "Endogenous mutations in human uncoupling protein 3 alter its functional properties", FEBS Lett., 1999 464:189-193.
Clapham, John C., et al., "Mice overexpressing human uncoupling protein-3 in skeletal muscle are hyperphagic and lean", Nature, Jul. 27, 2000, 406:415-418.
Fleury, Christophe, et al., "Uncoupling protein-2: a novel gene linked to obesity and hyperinsulinemia", Nature Genetics, Mar. 15, 1997, 15: 269-272.
Gong, Da-Wei, et al., "Lack of obesity and natural response to fasting and thyroid Hormone in Mice lacking Uncoupling Protein-3", J. Biol. Chem., May 26, 2000, 275:16251-16257.
Gura, Trisgha, "Uncoupling Proteins Provide New Clue to Obesity's Causes", Science, May 29, 1998, 280: ( Issue 5368) 1369-1370.
Millet, Laurence, et al., "Increased *Uncoupling Protein-2* and -3mRNA Expression during Fasting in Obese and Lean Human", J. Clin. Invest., Dec. 11, 1997, 100 (11): 2665-2670.
Naeger, Lisa K., et al., "Identification of a STAT4 Binding Site in the interleukin-12 Receptor Required for Signaling", J Biol Chem, Jan. 22, 1999, 274(4): 1875-1878.
Nicholls, D.G., et al., "Thermogenic Mechaisms in Brown Fat", Physiol. Review, 1984, 64(1):1-64.
Sanfilippo, Pauline J., "Novel Thiazole Based Heterocycles as inhibitors of LFA-1/ICAM-1 Mediated Cell Adhesion", J. Med. Chem., 1995, 38:1057-1059.
Scarpace, P.J., "UCP2, UCP3 are leptin gene expressin: modulation by food restriction and leptin", J. of Endocrinol., 1998, 159:349-357.
Surwit, Richard S., "Diet-induced changes in uncoupling proteins in obesity-prone and obesity-resistant strains of mice", Proc. Nat. Acad. Sci. USA, Mar. 1998, 95:4061-4065.
Vidal-Puig, Antonio J., et al., "Energy Metabolism in Uncoupling Protein 3 Gene Knockout Mice", J. Microbiol. Chem. May 26, 2000, 275 (21):16258-16266.
Vidal-Puig, Antonio J., et al., "UCP3: An uncoupling Protein Homologue Expressed Preferentially and Abundantly in Skeletal Muscle and Brown Adipose Tissue", Biochem. Biophys. Res. Comm., 1997, 235:79-82.
Walder, Ken, et al., "Association between uncoupling protein polymorphisms (UCP2-UCP3) and energy metabolism/obesity in Pima Indians", Hum. Molec. Genet., 1998, 7(9):1431-1435.

* cited by examiner

*Primary Examiner*—Kamal A. Saeed
*Assistant Examiner*—Jason M Nolan
(74) *Attorney, Agent, or Firm*—Christopher J. Smith

(57) ABSTRACT

Compounds, compositions and methods are provided that are useful in the treatment or prevention of a condition or disorder mediated by an uncoupling protein. In particular, the compounds of the invention modulate the expression and/or activity of UCP3. The subject compositions are particularly useful in the treatment of obesity and type II diabetes, and associated diseases
1
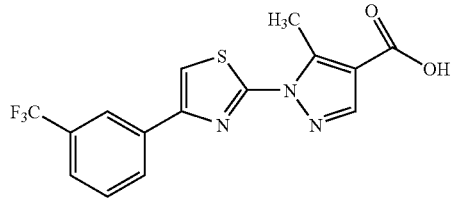
2
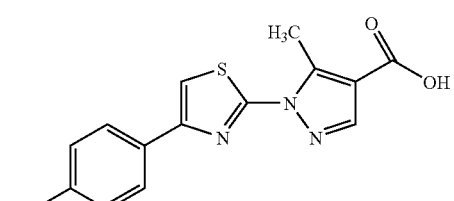
3
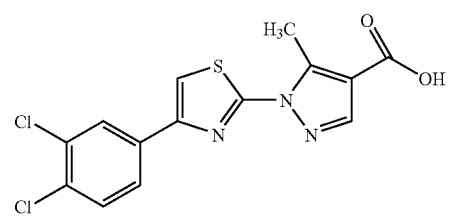
4
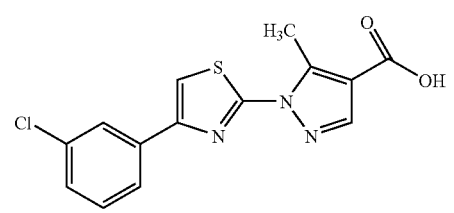
5
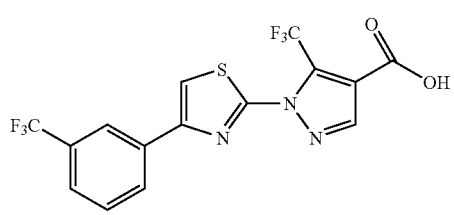
6
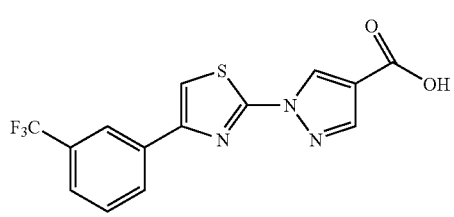
7
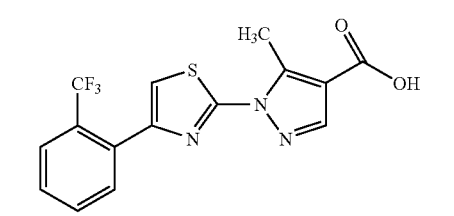
-continued
8
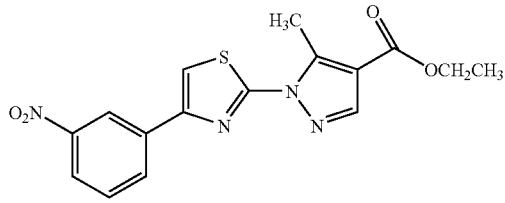
9
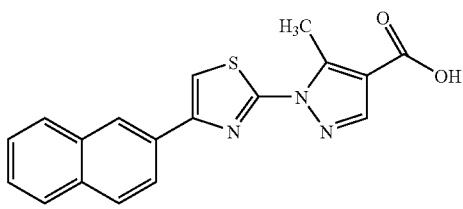
10
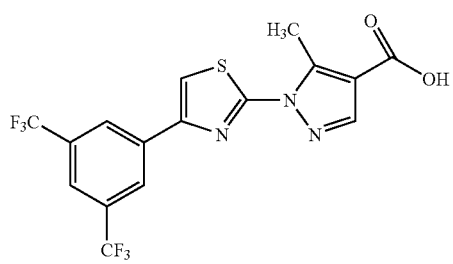
11
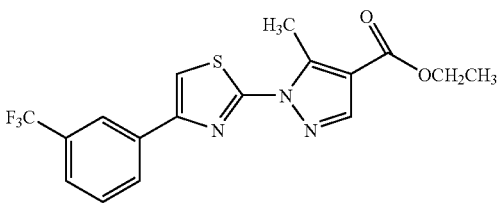
12
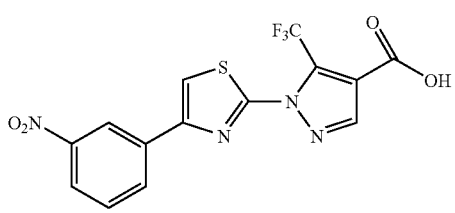
13
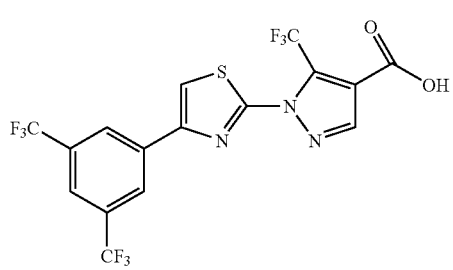
14
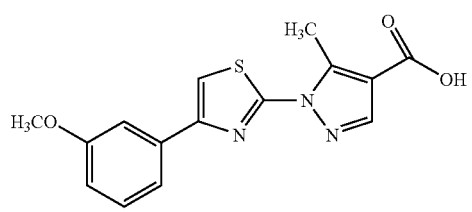

-continued
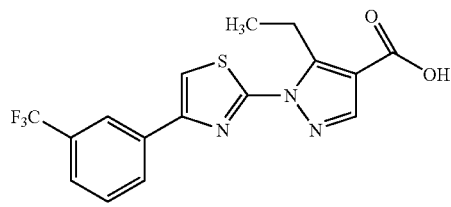
15
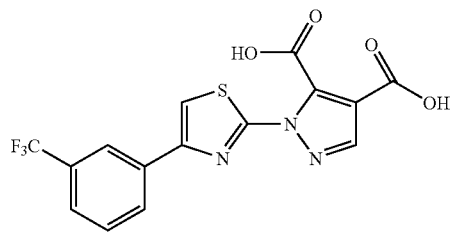
16
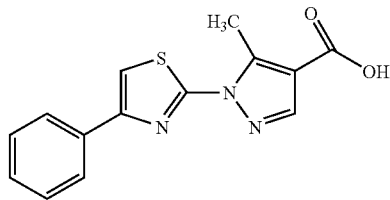
17
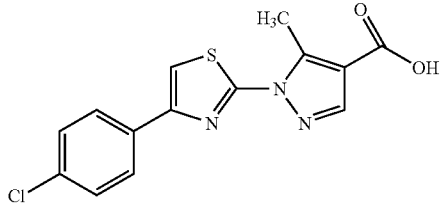
18
-continued
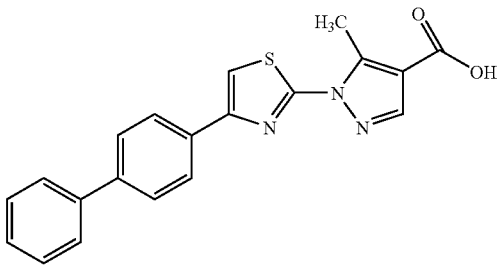
19
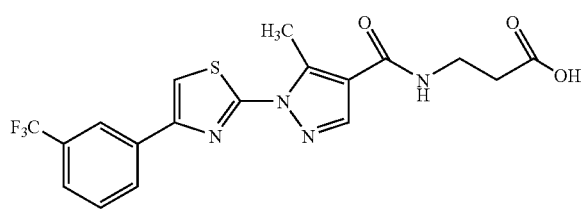
20
21 Claims, 1 Drawing Sheet

SEQUENCE LISTING

```
<160> NUMBER OF SEQ ID NOS: 21

<210> SEQ ID NO 1
<211> LENGTH: 15
<212> TYPE: DNA
<213> ORGANISM: Artificial
<220> FEATURE:
<223> OTHER INFORMATION: QPCR Primer or Probe Sequence

<400> SEQUENCE: 1
tgacctgcgc ccagc                                                    15

<210> SEQ ID NO 2
<211> LENGTH: 18
<212> TYPE: DNA
<213> ORGANISM: Artificial
<220> FEATURE:
<223> OTHER INFORMATION: QPCR Primer or Probe Sequence

<400> SEQUENCE: 2
cccaggcgta tcatggct                                                 18

<210> SEQ ID NO 3
<211> LENGTH: 25
<212> TYPE: DNA
<213> ORGANISM: Artificial
<220> FEATURE:
<223> OTHER INFORMATION: QPCR Primer or Probe Sequence

<400> SEQUENCE: 3
cacggatgtg gtgaaggtcc gattt                                         25

<210> SEQ ID NO 4
<211> LENGTH: 20
<212> TYPE: DNA
<213> ORGANISM: Artificial
<220> FEATURE:
<223> OTHER INFORMATION: QPCR Primer or Probe Sequence

<400> SEQUENCE: 4
aaagtggaga ttgttgccat                                               20

<210> SEQ ID NO 5
<211> LENGTH: 19
<212> TYPE: DNA
<213> ORGANISM: Artificial
<220> FEATURE:
```

```
<223> OTHER INFORMATION: QPCR Primer or Probe Sequence

<400> SEQUENCE: 5
ttgactgtgc cgttgaatt                                                    19

<210> SEQ ID NO 6
<211> LENGTH: 26
<212> TYPE: DNA
<213> ORGANISM: Artificial
<220> FEATURE:
<223> OTHER INFORMATION: QPCR Primer or Probe Sequence

<400> SEQUENCE: 6
catgttccag tatgactcca ctcacg                                            26

<210> SEQ ID NO 7
<211> LENGTH: 20
<212> TYPE: DNA
<213> ORGANISM: Artificial
<220> FEATURE:
<223> OTHER INFORMATION: QPCR Primer or Probe Sequence

<400> SEQUENCE: 7
ccctgccctt tgtacacacc                                                   20

<210> SEQ ID NO 8
<211> LENGTH: 19
<212> TYPE: DNA
<213> ORGANISM: Artificial
<220> FEATURE:
<223> OTHER INFORMATION: QPCR Primer or Probe Sequence

<400> SEQUENCE: 8
cgatccgagg gcctcacta                                                    19

<210> SEQ ID NO 9
<211> LENGTH: 26
<212> TYPE: DNA
<213> ORGANISM: Artificial
<220> FEATURE:
<223> OTHER INFORMATION: QPCR Primer or Probe Sequence

<400> SEQUENCE: 9
cccgtcgcta ctaccgattg gatggt                                            26

<210> SEQ ID NO 10
<211> LENGTH: 20
<212> TYPE: DNA
<213> ORGANISM: Artificial
<220> FEATURE:
<223> OTHER INFORMATION: QPCR Primer or Probe Sequence

<400> SEQUENCE: 10
ggcagtgacc tgtgctcaac                                                   20

<210> SEQ ID NO 11
<211> LENGTH: 18
<212> TYPE: DNA
<213> ORGANISM: Artificial
<220> FEATURE:
<223> OTHER INFORMATION: QPCR Primer or Probe Sequence

<400> SEQUENCE: 11
cccaggcgta tcatggct                                                     18
```

<210> SEQ ID NO 12
<211> LENGTH: 25
<212> TYPE: DNA
<213> ORGANISM: Artificial
<220> FEATURE:
<223> OTHER INFORMATION: QPCR Primer or Probe Sequence

<400> SEQUENCE: 12
cacggatgtg gtgaaggtcc gattt                                 25

<210> SEQ ID NO 13
<211> LENGTH: 20
<212> TYPE: DNA
<213> ORGANISM: Artificial
<220> FEATURE:
<223> OTHER INFORMATION: QPCR Primer or Probe Sequence

<400> SEQUENCE: 13
ccctgccctt tgtacacacc                                       20

<210> SEQ ID NO 14
<211> LENGTH: 19
<212> TYPE: DNA
<213> ORGANISM: Artificial
<220> FEATURE:
<223> OTHER INFORMATION: QPCR Primer or Probe Sequence

<400> SEQUENCE: 14
cgatccgagg gcctcacta                                        19

<210> SEQ ID NO 15
<211> LENGTH: 26
<212> TYPE: DNA
<213> ORGANISM: Artificial
<220> FEATURE:
<223> OTHER INFORMATION: QPCR Primer or Probe Sequence

<400> SEQUENCE: 15
cccgtcgcta ctaccgattg gatggt                                26

<210> SEQ ID NO 16
<211> LENGTH: 20
<212> TYPE: DNA
<213> ORGANISM: Artificial
<220> FEATURE:
<223> OTHER INFORMATION: QPCR Primer or Probe Sequence

<400> SEQUENCE: 16
ggcagtgacc tgtgctcaac                                       20

<210> SEQ ID NO 17
<211> LENGTH: 18
<212> TYPE: DNA
<213> ORGANISM: Artificial
<220> FEATURE:
<223> OTHER INFORMATION: QPCR Primer or Probe Sequence

<400> SEQUENCE: 17
cccaggcgta tcatggct                                         18

<210> SEQ ID NO 18
<211> LENGTH: 25
<212> TYPE: DNA
<213> ORGANISM: Artificial
<220> FEATURE:
<223> OTHER INFORMATION: QPCR Primer or Probe Sequence

```
-continued

<400> SEQUENCE: 18
cacggatgtg gtgaaggtcc gattt                                           25

<210> SEQ ID NO 19
<211> LENGTH: 20
<212> TYPE: DNA
<213> ORGANISM: Artificial
<220> FEATURE:
<223> OTHER INFORMATION: QPCR Primer or Probe Sequence

<400> SEQUENCE: 19
ccctgccctt tgtacacacc                                                 20

<210> SEQ ID NO 20
<211> LENGTH: 19
<212> TYPE: DNA
<213> ORGANISM: Artificial
<220> FEATURE:
<223> OTHER INFORMATION: QPCR Primer or Probe Sequence

<400> SEQUENCE: 20
cgatccgagg gcctcacta                                                  19

<210> SEQ ID NO 21
<211> LENGTH: 26
<212> TYPE: DNA
<213> ORGANISM: Artificial
<220> FEATURE:
<223> OTHER INFORMATION: QPCR Primer or Probe Sequence

<400> SEQUENCE: 21
cccgtcgcta ctaccgattg gatggt                                          26
```

BIS-ARYL THIAZOLE DERIVATIVES

CROSS-REFERENCE TO RELATED APPLICATIONS

This application is a national phase application of International Application No. PCT/US02/20447, filed Jun 27, 2002, which claims the benefit of U.S. Provisional Application No. 60/302,193, filed Jun. 29, 2001.

FIELD OF THE INVENTION

The present invention relates to compounds that modulate UCP3 expression and/or activity and are useful in the treatment of conditions and disorders mediated by UCP3.

BACKGROUND OF THE INVENTION

A mitochondrial protein called uncoupling protein 1 (UCP1) is thought to play an important role in the body's regulation of energy utilization. Such regulation provides widespread physiological controls, including body weight, appetite, glucose metabolism, temperature, immune responses, etc. Mechanistically, UCP1 is thought to create a pathway that allows dissipation of the proton electrochemical gradient across the inner mitochondrial membrane in brown adipose tissue, without coupling to any other energy consuming process (for review, see Nicholis & Locke (1984) *Physiol. Rev.* 64:1-64). Unfortunately, the role of UCP1 in physiologies, such as body weight regulation in large adult mammals, such as humans, cattle, pigs, etc., is likely to be limited, since there is little brown adipose tissue in such animals.

UCP2 is a second, related uncoupling protein that is much more widely expressed in large adult mammals (see, e.g. Fleury et al. (1997) *Nat. Genet.* 15:269-272 and Tartaglia et al. WO 96/05861). Consistent with a role in the regulation of energy utilization in general, and in diabetes and obesity in particular, the UCP2 gene is upregulated in response to fat feeding and maps to regions of the human and mouse genomes linked to hyperinsulinaemia and obesity.

More recently, a third structurally related UCP gene, UCP3 has been characterized and found to be preferentially expressed in skeletal muscle and brown adipose tissues; see Vidal-Puig et al. (1997) *Biochem. Biophys. Res. Comm.* 235:79-82 and Boss et al. (1997) *FEBS Lett.* 408:39-42. UCP3 has been linked to a number of disorders associated with the control of energy expenditure, including obesity and diabetes.

The identification of compounds that modulate the activity and/or expression of UCP3 represents an attractive approach to the development of therapeutic agents for the treatment of conditions and disorders associated with energy utilization.

SUMMARY OF THE INVENTION

The present invention provides methods of using bis-aryl thiazole compounds and compositions to treat conditions and disorders mediated by UCP3. In particular, the present invention provides methods for treating obesity and diabetes.

The methods of the invention comprise administering to a subject in need thereof a therapeutically effective amount of a compound of formula (1):

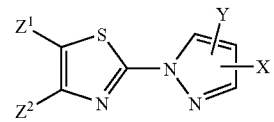

I wherein X is selected from the group consisting of $CO_2R^1$ and $C(O)NR^1R^2$, Y is selected from the group consisting of hydrogen, $(C_1-C_4)$alkyl, fluoro$(C_1-C_4)$alkyl, aryl, heteroaryl, halogen, $NR^3R^4$ and $CO_2R^3$, $Z^1$ is selected from the group consisting of hydrogen, $(C_1-C_4)$alkyl and halogen, and $Z^2$ is selected from the group consisting of aryl and heteroaryl, or $Z^1$ and $Z^2$ may be combined to form a fused 6-membered ring. $R^1$, $R^2$, $R^3$ and $R^4$ are independently selected from the group consisting of hydrogen, $(C_1-C_4)$alkyl, carboxy$(C_1-C_4)$alkyl and aryl.

The invention also provides methods for treating a condition or disorder mediated by UCP3.

The invention further provides methods for treating a condition or disorder mediated by a nuclear hormone receptor transcription factor.

The present invention also provides pharmaceutical compositions comprising a pharmaceutically acceptable carrier or excipient in combination with a compound of formula (I):

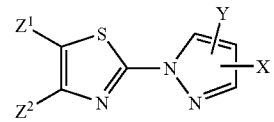

I wherein X is selected from $CO_2R^1$ and $C(O)NR^1R^2$, Y is selected from hydrogen, $(C_1-C_4)$alkyl, fluoro$(C_1-C_4)$alkyl, aryl, heteroaryl, halogen, $NR^3R^4$ and $CO_2R^3$, $Z^1$ is selected from hydrogen, $(C_1-C_4)$alkyl and halogen, and $Z^2$ is selected from aryl and heteroaryl, or $Z^1$ and $Z^2$ may be combined to form a fused 6-membered ring. $R^1$, $R^2$, $R^3$ and $R^4$ are independently selected from hydrogen, $(C_1-C_4)$alkyl, carboxy$(C_1-C_4)$alkyl and aryl.

The present invention also provides compounds of formula (I):

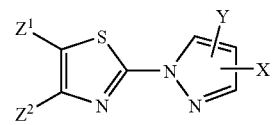

I wherein X is selected from $CO_2R^1$ and $C(O)NR^1R^2$, Y is selected from hydrogen, $(C_1-C_4)$alkyl, fluoro$(C_1-C_4)$alkyl, aryl, heteroaryl, halogen, $NR^3R^4$ and $CO_2R^3$, $Z^1$ is selected from hydrogen, $(C_1-C_4)$alkyl and halogen, $Z^2$ is selected from aryl and heteroaryl, or $Z^1$ and $Z^2$ may be combined to form a fused 6-membered ring, and $R^1$, $R^2$, $R^3$ and $R^4$ are independently selected from hydrogen, $(C_1-C_4)$alkyl, carboxy$(C_1-C_4)$alkyl and aryl, provided that the compound is not 1-[4-(3-(trifluoromethyl)phenyl)thiazol-2-yl]-5-methylpyrazole-4-carboxylic acid, 1-[4-(3-(trifluoromethyl)phenyl)thiazol-2-yl]-5-trifluoromethylpyrazole-4-carboxylic acid, 1-[4-(3-methoxyphenyl)thiazol-2-yl]-5-trifluoromethylpyrazole-4-carboxylic acid, 1-[4-(4-chlorophenyl)thiazol-2-yl]-5-trifluoromethylpyrazole-4-carboxylic acid, 1-[4-(4-nitrophenyl)thiazol-2-yl]-5-trifluoromethylpyrazole-4-carboxylic acid, 1-[4-(3-(trifluoromethyl)phenyl)-5-bromothiazol-2-yl]-5-trifluoromethylpyrazole-4-carboxylic acid, 1-[4-(3-methylphenyl)thiazol-2-yl]-5-trifluoromethylpyrazole-4-carboxylic acid, 1-[4-(4-(trifluoromethyl)phenyl)thiazol-2-yl]-5-trifluoromethylpyrazole-4-carboxylic acid, 1-[4-(2-(trifluoromethyl)phenyl)thiazol-2-yl]-5-trifluoromethylpyrazole-4-carboxylic acid, 1-[4-(3-chlorophenyl)thiazol-2-yl]-5-trifluoromethylpyrazole-4-carboxylic acid, or 1-[4-(3-(trifluoromethyl)phenyl)thiazol-2-yl]-5-phenylpyrazole-4-carboxylic acid.

Unless otherwise indicated, the compounds provided in the above formulas are meant to include pharmaceutically acceptable salts and prodrugs thereof.

Other objects, features and advantages of the present invention will become apparent to those skilled in the art from the following description and claims.

DETAILED DESCRIPTION OF THE INVENTION

Abbreviations and Definitions

Figure 1:
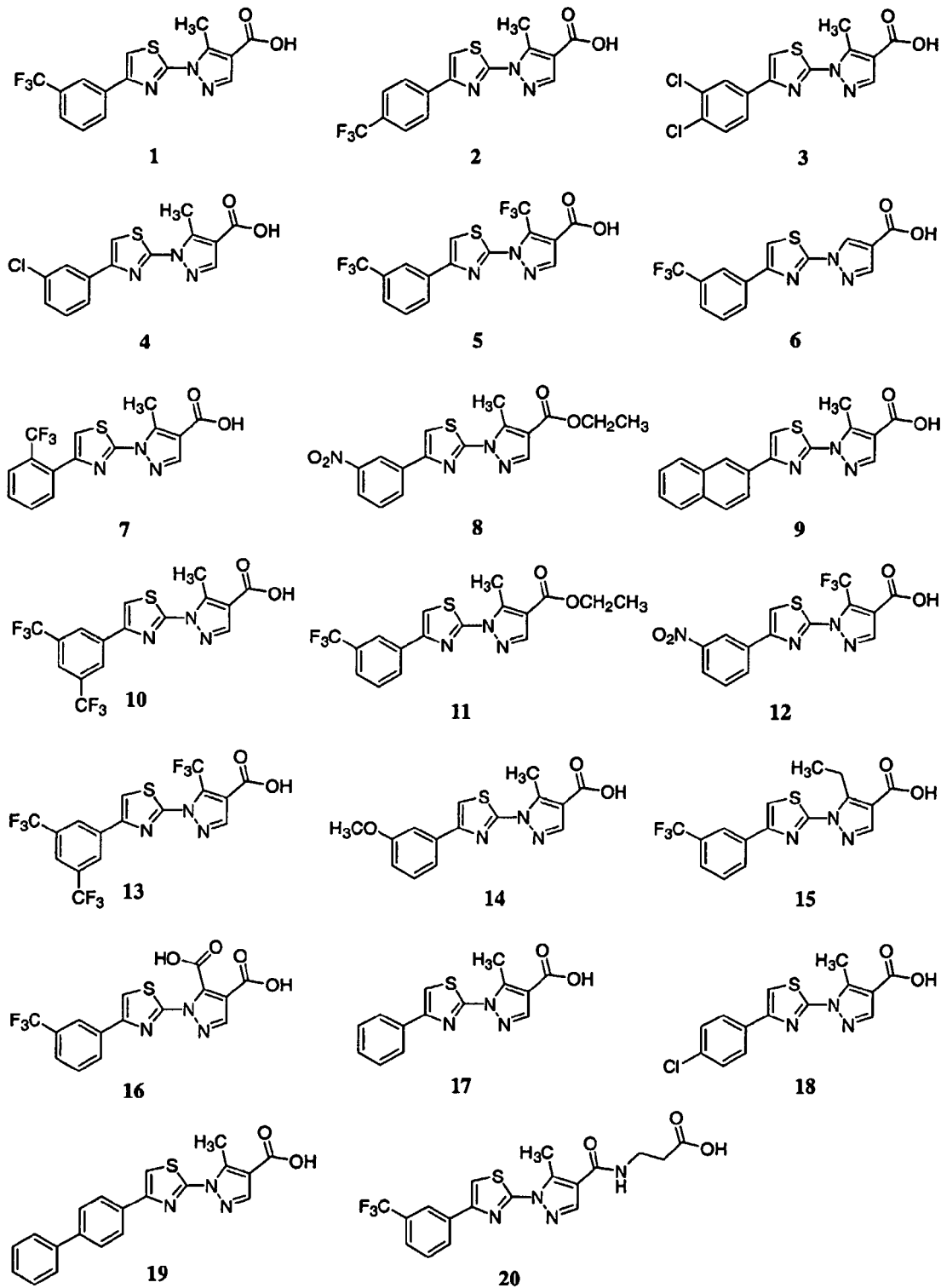
FIG. 1 provides the structures of exemplary compounds of formula I.

The abbreviations used herein are conventional, unless otherwise defined.

"UCP3", as used herein, refers to the UCP3 protein, unless otherwise stated.

The terms "treat", "treating" and "treatment" refer to a method of alleviating or abrogating a disease and/or its attendant symptoms.

The terms "prevent", "preventing" and "prevention" refer to a method of decreasing the probability or eliminating the possibility that a disease will be contracted.

As used herein, the term "UCP3-mediated condition or disorder" and the like refers to a condition or disorder characterized by inappropriate, e.g., less than or greater than normal, UCP3 functional activity. Inappropriate UCP3 functional activity might arise as the result of decreased UCP3 expression (leading to, e.g., obesity or diabetes) or increased UCP3 expression. A UCP3-mediated condition or disorder may be completely or partially mediated by inappropriate UCP3 activity. However, a UCP3-mediated condition or disorder is one in which modulation of UCP3 results in some effect on the underlying condition or disease (e.g., a UCP3 agonist results in some improvement in patient well-being in at least some patients).

As used herein, the term "nuclear hormone receptor-mediated condition or disorder" and the like refers to a condition or disorder characterized by inappropriate, e.g., less than or greater than normal, functional activity of a particular nuclear hormone receptor. Inappropriate nuclear hormone receptor functional activity might arise as the result of decreased nuclear hormone receptor expression or increased nuclear hormone receptor expression. A nuclear hormone receptor-mediated condition or disorder may be completely or partially mediated by inappropriate nuclear hormone receptor activity. However, a nuclear hormone receptor-mediated condition or disorder is one in which modulation of nuclear hormone receptor results in some effect on the underlying condition or disease (e.g., a nuclear hormone receptor agonist results in some improvement in patient well-being in at least some patients).

The term "therapeutically effective amount" refers to that amount of the compound being administered sufficient to prevent development of or alleviate to some extent one or more of the symptoms of the disease being treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, "obesity" refers to the excessive accumulation of body fat. Obesity may have genetic, environmental (e.g., expending less energy than is consumed) and regulatory determinants. Hypertension and lipid disorders, such as, hyperlidemia and coronary artery disease, are commonly associated with obesity.

As used herein, "diabetes" refers to type II diabetes mellitus (non-insulin-dependent diabetes mellitus or NIDDM). NIDDM is characterized by insulin resistance and hyperglycemia. Obesity and lipid disorders are commonly associated with NIDDM.

The term "modulate" refers to the ability of a compound to increase or decrease the expression and/or activity of UCP3. Modulation, as described herein, includes the inhibition or activation of UCP3 and/or the downregulation or upregulation of UCP3 expression, either directly or indirectly. A modulator preferably downregulates UCP3 expression and/or inhibits UCP3. More preferably, a modulator upregulates or downregulates UCP3 expression and/or activates or inhibits UCP3. Most preferably, a modulator upregulates UCP3 expression and/or activates UCP3.

The term "alkyl", by itself or as part of another substituent, means, unless otherwise stated, a straight or branched chain, or cyclic hydrocarbon radical, or combination thereof, which may be fully saturated, mono- or polyunsaturated and can include di- and multi-valent radicals, having the number of carbon atoms designated (i.e., $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl," "cycloalkyl" and "alkylene."

The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

Preferably, the term "($C_1$-$C_4$)alkyl" refers to a saturated straight or branched hydrocarbon chain having from 1 to 4 carbon atoms. Examples of particular values for "($C_1$-$C_4$) alkyl" include methyl, ethyl, propyl, 2-propyl, butyl, etc.

Unless otherwise indicated, the name of a specific alkyl group as used herein, refers to the straight chain or unbranched isomer.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si(CH3)3, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkyle groups, heteroatoms can also occupy either or both of the chain termini. Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl. For example, the term "halo ($C_1$-$C_4$)alkyl" is meant to include trifluoromethyl, 2,2,2-trifluoroethyl, 4-chlorobutyl, 3-bromopropyl, and the like.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a heteroatom. Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below.

Preferably, the term "aryl" refers to a phenyl or naphthyl group which is unsubstituted or substituted by one, two or three substitutents selected independently, described below.

Preferably, the term "heteroaryl" refers to a pyrrolyl, pyrazolyl, imidazolyl, pyrazinyl, oxazolyl, isoxazolyl, thiazolyl, furyl, thienyl, pyridyl, pyrimidyl, benzothiazolyl, purinyl, benzimidazolyl, indolyl, isoquinolyl, quinoxalinyl, quinoxalinyl, quinolyl or quinolyl group which is unsubstituted or substituted by one, two or three substitutents selected independently, described below.

The term "arylalkyl" is meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R" R'", —OC(O)R', —C(O)R', —$CO_2R^1$ (e.g., carboxyl, carboxyalkyl), —CONR'R" (e.g., carbamoyl, carboxamido), —OC(O)NR'R", —NR"C(O)R', —NR'—C(O)NR"R'", —NR"C(O)2R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$ in a number ranging from zero to (2N+1), where N is the total number of carbon atoms in such radical. R', R" and R'" each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like). Preferably, the alkyl groups will have from 0 to 3 substituents.

Similarly, substituents for the aryl and heteroaryl groups are varied and are selected from: -halogen, —OR', —OC(O)R', —NR'R", —SR', —R', —CN, —$NO_2$, —$CO_2$R' (e.g., carboxyl, carboxyalkyl), —CONR'R" (e.g., carbamoyl, carboxamido), —C(O)R', —OC(O)NR'R", —NR"C(O)R', —NR"C(O)2R', —NR'—C(O)NR"R'", —NH—C(NH2)=NH, —NR'C($NH_2$)=NH, —NH—C($NH_2$)=NR', —S(O)R', —S(O)$_2$R', —S(O)$_2$NR'R", —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl, (unsubstituted aryl)-($C_1$-$C_4$) alkyl, and (unsubstituted aryl)oxy-($C_1$-$C_4$)alkyl.

Two of the substituents on adjacent atoms of the aryl ring may optionally be replaced with a substituent of the formula -T-C(O)—($CH_2$)$_q$—U—, wherein T and U are independently —NH—, —O—, —$CH_2$— or a single bond, and q is an integer of from 0 to 2. Alternatively, two of the substituents on adjacent atoms of the aryl ring may optionally be replaced with a substituent of the formula -A-($CH_2$)$_r$—B—, wherein A and B are independently —$CH_2$—, —O—, —NH—, —S—, —S(O)—, —S(O)$_2$—, —S(O)$_2$NR'— or a single and r is an integer of from 1 to 3. One of the single bonds of the new ring so formed may optionally be replaced with a double bond. Alternatively, two of the substituents on adjacent atoms of the aryl ring may optionally be replaced with a substituent of the formula —($CH_2$)$_s$—X—($CH_2$)$_t$—, where s and t are independently integers of from 0 to 3, and X is —O—, —NR'—, —S—, —S(O)—, —S(O)$_2$—, or —S(O)$_2$NR'—. The substituent R'- in —NR'— and —S(O)$_2$NR'— is selected from hydrogen or unsubstituted ($C_1$-$C_6$) alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactouronric acids and the like (see, for example, Berge, S. M., et al. (1977) *J. Pharm. Sci.* 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Embodiments of the Invention

UCP3 is an attractive target for anti-obesity and/or anti-diabetic drug development. Human UCP3 has been described (see GenBank Accession No. P55916). Mouse and bovine UCP3 have also been described (see GenBank Accession Nos. P56501 and O77792, respectively). Regulators of UCP3 gene expression have been described; see, e.g., U.S. Pat. No. 5,849,581, which reference is incorporated by reference herein. Modulation of UCP3 expression and/or activity, e.g., upregulation of UCP3 expression and/or activation of UCP3, is one approach to altering energy balance, e.g., increasing energy expenditure relative to energy consumption. The compounds of the present invention upregulate UCP3 expression and/or activity, and thus, are useful in, for example, the treatment or prevention of obesity.

Methods of Use

In one aspect, the present invention provides novel methods for using compounds of formula (I):

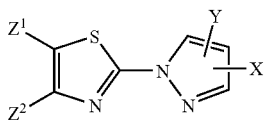

I wherein X is selected from $CO_2R^1$ and $C(O)NR^1R^2$, Y is selected from hydrogen, $(C_1-C_4)$alkyl, fluoro$(C_1-C_4)$alkyl, aryl, heteroaryl, halogen, $NR^3R^4$ and $CO_2R^3$, $Z^1$ is selected from hydrogen, $(C_1-C_4)$alkyl and halogen, $Z^2$ is selected from aryl and heteroaryl, or $Z^1$ and $Z^2$ may be combined to form a fused 6-membered ring, and $R^1$, $R^2$, $R^3$ and $R^4$ are independently selected from hydrogen, $(C_1-C_4)$alkyl, carboxy$(C_1-C_4)$alkyl and aryl, and compositions thereof.

One of skill in the art will understand that a number of structural isomers are represented by formula I. Preferred isomers are those having the structural orientation represented by formula (II):

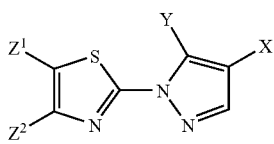

II

In one group of preferred embodiments, X is $CO_2R^1$. In particularly preferred embodiments, X is $CO_2R^1$ and $R^1$ is H. Examples of particular values for X within this group of preferred embodiments are carboxyl, and carboxyethyl.

In another group of preferred embodiments, X is $C(O)NR^1R^2$. Examples of particular values for X within this group are $CONH_2$, $C(O)NHCH_3$, $C(O)NH—(CH_2)_2—CO_2H$ and $C(O)NH—(CH_2)_3—CO_2H$.

In another group of preferred embodiments, Y is hydrogen, $(C_1-C_4)$alkyl or fluoro$(C_1-C_4)$alkyl. In particularly preferred embodiments, Y is $(C_1-C_4)$alkyl. Examples of particular values for Y are methyl, ethyl, trifluoromethyl and carboxyl.

In another group of preferred embodiments, $Z^1$ is hydrogen.

In yet another group of preferred embodiments, $Z^2$ is aryl. Particularly preferred are embodiments in which $Z^2$ is phenyl or naphthyl. Examples of particular values for $Z^2$ within this group of preferred embodiments are 2-trifluoromethylphenyl, 3-trifluoromethylphenyl, 4-trifluoromethylphenyl, 3,5-bis(trifluoromethyl)phenyl, 3-nitrophenyl, 3-methoxyphenyl, 3-chlorophenyl, 4-chlorophenyl, 3,4-dichlorophenyl, biphenyl and 2-naphthyl.

In still another group of preferred embodiments, $Z^2$ is heteroaryl. Particularly preferred are embodiments in which $Z^2$ is pyridyl or pyrimidinyl.

In another group of preferred embodiments, $Z^1$ and $Z^2$ are combined to form a fused 6-membered ring. Particularly preferred are embodiments in $Z^1$ and $Z^2$ are combined to form a fused benzene ring.

Another group of preferred embodiments has the formula (III):

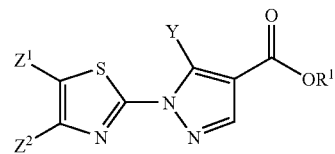

III

In compounds of formula III, $R^1$, Y, $Z^1$ and $Z^2$ have the meanings and preferred groupings provided above.

Yet another group of preferred embodiments is represented by the formula (IV):

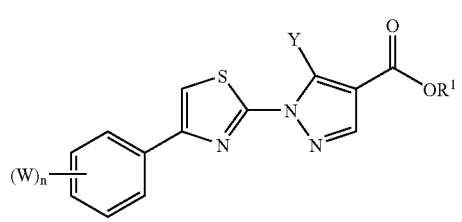

IV

In compounds of formula IV, W is $(C_1-C_4)$alkyl, fluoro$(C_1-C_4)$alkyl, halogen or nitro, n is an integer from 1-3 and $R^1$ and Y have the meanings and preferred groupings provided above.

Still another group of preferred embodiments is represented by the formula (V):

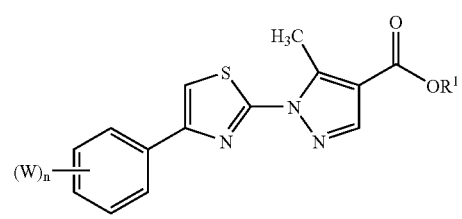

V wherein $R^1$, W and n have the meanings and preferred groupings provided above. An exemplary compound of formula V is:

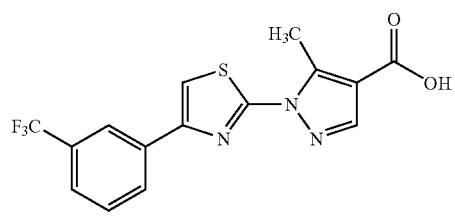

1

Still another group of preferred embodiments is represented by the formula (VI):

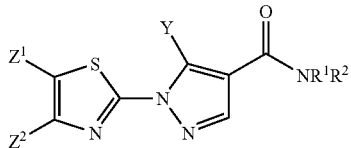

wherein $R^1$, $R^2$, Y, $Z^1$ and $Z^2$ have the meanings and preferred groupings provided above.

Still another group of preferred embodiments is represented by the formula (VII):

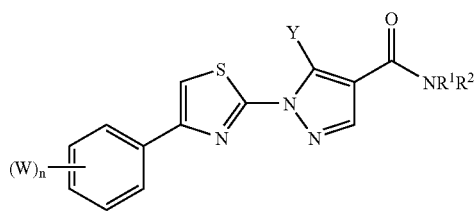

In compounds of formula VII, W is $(C_1-C_4)$alkyl, fluoro$(C_1-C_4)$alkyl, halogen or nitro, n is an integer from 1-3 and $R^1$ and Y have the meanings and preferred groupings provided above.

Yet another group of preferred embodiments is represented by the formula (VIII):

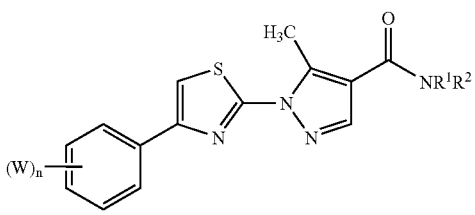

wherein $R^3$, $R^4$, W and n have the meanings and preferred groupings provided above. An exemplary compound of formula VIII is:

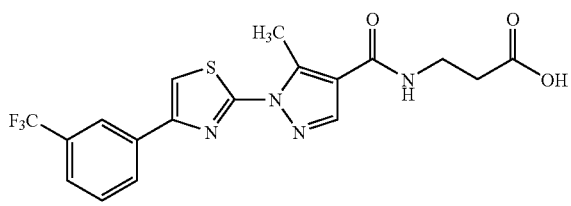

In particular, the invention provides novel methods for treating or preventing prevent a condition or disorder mediated by UCP3, such as obesity or diabetes. The subject methods may also be useful for treating or preventing a disease, disorder, dysfunction and the like, in which obesity or diabetes contributes to the pathogenesis thereof, such as atherosclerosis. The subject methods may also be useful for improving insulin sensitivity and/or reducing blood glucose, and reducing serum cholesterol levels. The methods typically involve administering to a patient a therapeutically effective amount of one or more of the compounds of formula I, II, III, IV, V, VI, VII or VIII, or compositions thereof.

The present invention also provides novel methods for using compounds of formula I, II, III, IV, V, VI, VII or VIII and compositions thereof to modulate UCP3. The methods typically involve contacting a cell with one or more of the subject compounds or compositions.

It is believed that the compounds of the invention modulate UCP3 expression and/or activity by specifically modulating UCP3 gene transcription. Transcription regulates UCP3 gene expression and is activated by the association of one or more transcription factors with a UCP3 transcriptional promoter. Therefore, modulating gene transcription, e.g., modulating the association of a transcription factor with a UCP3 transcriptional promoter, will modulate UCP3 gene expression and treat or prevent a UCP3-mediated condition or disorder. For example, enhancing the association of a transcription factor with a UCP3 transcriptional promoter will increase UCP3 gene transcription and upregulate UCP3 gene expression, leading to increased UCP3 transcript and/or protein levels (i.e., increased UCP3 mRNA and/or increased UCP3). The resulting increased UCP3 transcript and/or protein levels can be used to treat a subject deficient in functional UCP3.

While a precise understanding of the mechanism by which the compounds of the present invention modulate UCP3 gene transcription is not required in order to practice the invention, it is believed that the compounds interact, either directly or indirectly, with a transcription factor and modify the ability of the transcription factor to associate with the UCP3 promoter. In particular, it is believed that the compounds of the invention interact with a nuclear hormone receptor family transcription factor and modulate its activity.

Accordingly, the present invention provides novel methods for using the foregoing compounds and compositions to treat or prevent conditions and disorders mediated by a nuclear hormone receptor transcription factor, preferably retinoid X receptor (RXR). Nuclear hormone receptor transcription factors are soluble protein receptors that bind to specific cis-acting sequences in the promoter region of target genes and modulate gene expression in response to endogenous hormone activators or ligands. Nuclear hormone receptors have been shown to be involved in numerous pathologies, including metabolic diseases, cardiovascular diseases, lipid disorders and cell proliferative disorders. Exemplary RXR-mediated conditions and disorders include, but are not limited to, diabetes, atherosclerosis, hyperlipidemia, hypercholesterolemia, cell proliferative disorders such as cancers of the breast, skin, prostate, cervix, uterus, colon, bladder, esophagus, stomach, lung, larynx, oral cavity, blood and lymphatic system, skin proliferative disorders (e.g., psoriasis) and diseases of the eye (e.g., proliferative vitreoretinopathy).

The present invention further provides novel methods for using the foregoing compounds and compositions to modulate RXR. The methods typically involve contacting a cell with one or more of the subject compounds or compositions.

Compositions

In another aspect, the present invention provides pharmaceutical compositions which are suitable for pharmaceutical or diagnostic use. The compositions comprise compounds of formula I, II, III, IV, V, VI, VII or VIII, in combination with a diagnostically or pharmaceutically acceptable carrier or excipient. The subject compositions are useful for treating or preventing conditions and disorders mediated by UCP3, such as obesity and diabetes. The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of formula I, II, III, IV, V, VI, VII or VIII or a pharmaceutically acceptable salt of a compound of formula I, II, III, IV, V, VI, VII or VIII.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

In therapeutic use for the treatment of obesity or diabetes, the compounds utilized in the pharmaceutical method of the invention are administered at the initial dosage of about 0.001 mg/kg to about 100 mg/kg daily. A daily dose range of about 0.1 mg/kg to about 10 mg/kg is preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The compositions may be advantageously combined and/or used in combination with agents useful in the treatment and/or prevention of obesity and/or diabetes and pathologies associated therewith (e.g., hyperlipidemia, atherosclerosis). In many instances, administration of the subject compounds or compositions in conjunction with these alternative therapeutic agents enhances the efficacy of such agents. Accordingly, in some instances, the present compounds, when combined or administered in combination with anti-obesity and/or anti-diabetic agents, can be used in dosages which are less than the expected amounts when used alone, or less than the calculated amounts for combination therapy.

Suitable agents for combination therapy include those that are currently commercially available and those that are in development or will be developed. Exemplary agents useful in the treatment of obesity and/or diabetes include $\beta_3$ adrenergic receptor agonists, leptin or derivatives thereof, neuropeptide Y antagonists, insulin and derivatives thereof, hypoglycemic agents, such as sulfonylureas (e.g., meglinatide, tolbutamide, chlorpropamide, acetohexamide, tolazamide, glyburide, glipizide and glimepiride), antihyperglycemic agents, such as biguanides (e.g., metformin), α-glucosidase inhibitors (e.g., acarbose), insulin sensitizers, such as thiazolidinones (e.g., rosiglitazone (Avandia®), troglitazone (Rezulin®) and pioglitazone (Actos®)), and RXR agonists, such as bexarotene (Targretin®).

Exemplary agents useful in the treatment of atherosclerosis and complications thereof include cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), nicotinic acid (niacin), fibric acid derivatives (gemfibrozil, clofibrate, fenofibrate and benzafibrate), probucol and nitroglycerin, and calcium channel blockers (e.g., veraparnil, nicardipine, amlodipine, diltiazem and nifedipine).

Exemplary agents useful in the treatment of cell proliferative disorders and/or skin proliferative disorders include preparations of interferon alpha, e.g., interferon α 2b, and interferon beta, e.g., interferon β-1 α (Avonex®) and interferon β-1 β (Betaseron®), DNA-alkylating agents (e.g., cyclophosphamide, ifosfamide), antimetabolites (e.g., azathioprene, 6-mercaptopurine, methotrexate, a folate antagonist, and 5-fluorouracil, a pyrimidine antagonist), microtubule disruptors (e.g., vincristine, vinblastine, paclitaxel and coichicine), DNA intercalators (e.g., doxorubicin, daunomycin and cisplatin), DNA synthesis inhibitors such as hydroxyurea and hormone therapy (e.g., tamoxifen and flutamide) and RXR agonists, such as bexarotene (Targretin®).

Compounds

In another aspect, the present invention provides compounds which are represented by the formula (I):

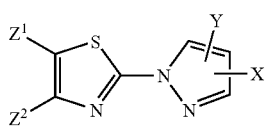

I wherein X is selected from $CO_2R^1$ and $C(O)NR^1R^2$, wherein $R^1$, $R^2$, $R^3$ and $R^4$ are independently selected from hydrogen, $(C_1-C_4)$alkyl, carboxy$(C_1-C_4)$alkyl and aryl, Y is selected from hydrogen, $(C_1-C_4)$alkyl, fluoro$(C_1-C_4)$alkyl, aryl, heteroaryl, halogen, $NR^3R^4$ and $CO_2R^3$, $Z^1$ is selected from hydrogen, $(C_1-C_4)$alkyl and halogen, and $Z^2$ is selected from aryl and heteroaryl, or $Z^1$ and $Z^2$ may be combined to form a fused 6-membered ring, with the proviso that the compound is not 1-[4-(3-(trifluoromethyl)phenyl)thiazol-2-yl]-5-methylpyrazole-4-carboxylic acid (1)

1-[4-(3-(trifluoromethyl)phenyl)thiazol-2-yl]-5-trifluoromethylpyrazole-4-carboxylic acid (5), 1-[4-(3-methoxyphenyl)thiazol-2-yl]-5-trifluoromethylpyrazole-4-carboxylic acid, 1-[4-(4-chlorophenyl)thiazol-2-yl]-5-trifluoromethylpyrazole-4-carboxylic acid, 1-[4-(4-nitrophenyl)thiazol-2-yl]-5-trifluoromethylpyrazole-4-carboxylic acid, 1-[4-(3-(trifluoromethyl)phenyl)-5-bromothiazol-2-yl]-5-trifluoromethylpyrazole-4-carboxylic acid, 1-[4-(3-methylphenyl)thiazol-2-yl]-5-trifluoromethylpyrazole-4-carboxylic acid, 1-[4-(4-(trifluoromethyl)phenyl)thiazol-2-yl]-5-trifluoromethylpyrazole-4-carboxylic acid, 1-[4-(2-(trifluoromethyl)phenyl)thiazol-2-yl]-5-trifluoromethylpyrazole-4-carboxylic acid, 1-[4-(3-chlorophenyl)thiazol-2-yl]-5-trifluoromethylpyrazole-4-carboxylic acid, or 1-[4-(3-(trifluoromethyl)phenyl)thiazol-2-yl]-5-phenylpyrazole-4-carboxylic acid.

One of skill in the art will understand that a number of structural isomers are represented by formula I. Preferred isomers are those having the structural orientation represented by formula (II):

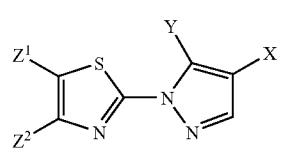

II

In one group of preferred embodiments, X is $CO_2R'$. In particularly preferred embodiments, X is $CO_2R^1$ and $R^1$ is H. Examples of particular values for X within this group of preferred embodiments are carboxyl, and carboxyethyl.

In another group of preferred embodiments, X is $C(O)NR^1R^2$. Examples of particular values for X within this group are $CONH_2$, $C(O)NHCH_3$, $C(O)NH$—$(CH_2)_2$—$CO_2H$ and $C(O)NH$—$(CH_2)_3$—$CO_2H$.

In another group of preferred embodiments, Y is hydrogen, $(C_1-C_4)$alkyl or fluoro$(C_1-C_4)$alkyl. In particularly preferred embodiments, Y is $(C_1-C_4)$alkyl. Examples of particular values for Y are methyl, ethyl, trifluoromethyl and carboxyl.

In another group of preferred embodiments, $Z^1$ is hydrogen.

In yet another group of preferred embodiments, $Z^2$ is aryl. Particularly preferred are embodiments in which $Z^2$ is phenyl or naphthyl. Examples of particular values for $Z^2$ within this group of preferred embodiments are 2-trifluoromethylphenyl, 3-trifluoromethylphenyl, 4-trifluoromethylphenyl, 3,5-bis(trifluoromethyl)phenyl, 3-nitrophenyl, 3-methoxyphenyl, 3-chlorophenyl, 4-chlorophenyl, 3,4-dichlorophenyl, biphenyl and 2-naphthyl.

In still another group of preferred embodiments, $Z^2$ is heteroaryl. Particularly preferred are embodiments in which $Z^2$ is pyridyl or pyrimidinyl.

In another group of preferred embodiments, $Z^1$ and $Z^2$ are combined to form a fused 6-membered ring. Particularly preferred are embodiments in $Z^1$ and $Z^2$ are combined to form a fused benzene ring.

Another group of preferred embodiments has the formula (III):

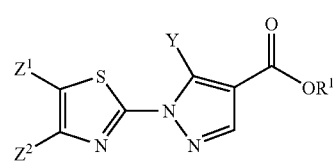

III

In compounds of formula III, $R^1$, Y, $Z^1$ and $Z^2$ have the meanings and preferred groupings provided above.

Yet another group of preferred embodiments is represented by the formula (IV):

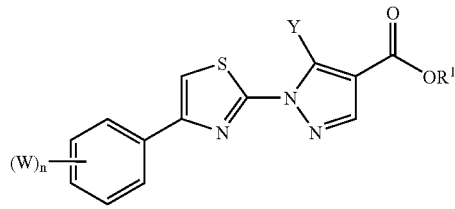

IV

In compounds of formula IV, W is $(C_1-C_4)$alkyl, fluoro$(C_1-C_4)$alkyl, halogen or nitro, n is an integer from 1-3 and $R^1$ and Y have the meanings and preferred groupings provided above.

Still another group of preferred embodiments is represented by the formula (V):

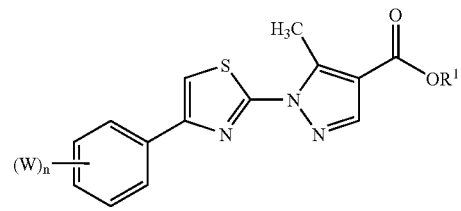

V wherein $R^1$, W and n have the meanings and preferred groupings provided above.

Still another group of preferred embodiments is represented by the formula (VI):

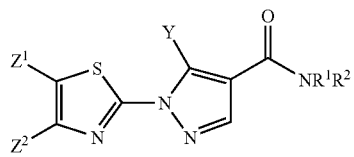

VI wherein $R^3$, $R^4$, Y, $Z^1$ and $Z^2$ have the meanings and preferred groupings provided above.

Still another group of preferred embodiments is represented by the formula (VII):

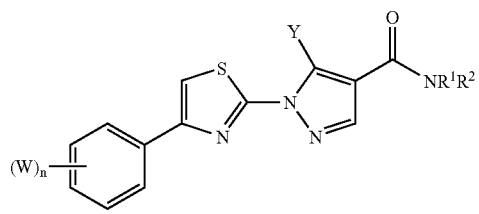

VII

In compounds of formula VII, W is $(C_1-C_4)$alkyl, fluoro$(C_1-C_4)$alkyl, halogen or nitro, n is an integer from 1-3 and $R^3$, $R^4$ and Y have the meanings and preferred groupings provided above.

Yet another group of preferred embodiments is represented by the formula (VIII):

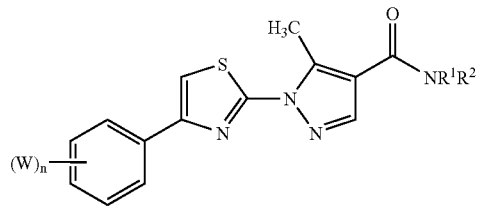

VIII wherein $R^3$, $R^4$, W and n have the meanings and preferred groupings provided above. An exemplary compound of formula VIII is:

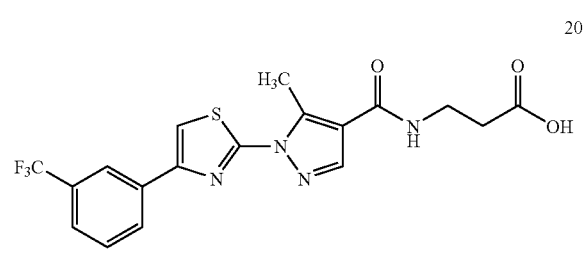

20

Preparation of the Compounds

The compounds of the present invention can be prepared using standard synthetic methods. Scheme 1 illustrates an exemplary method for the preparation of compounds of structural formula I. One of skill in the art will understand that the synthesis provided below can be modified to use different starting materials and alternate reagents to prepare compounds in the other structural classes. Accordingly, Scheme 1 is expressed as a non-limiting embodiment.

SCHEME 1

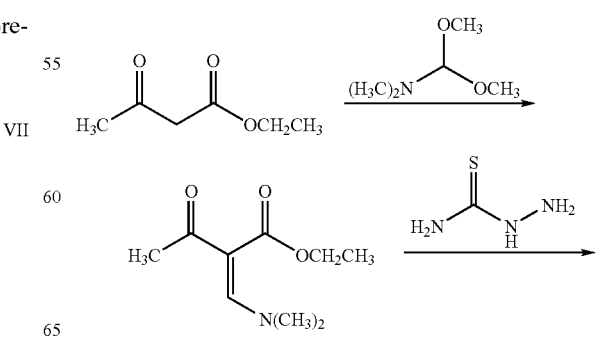

-continued

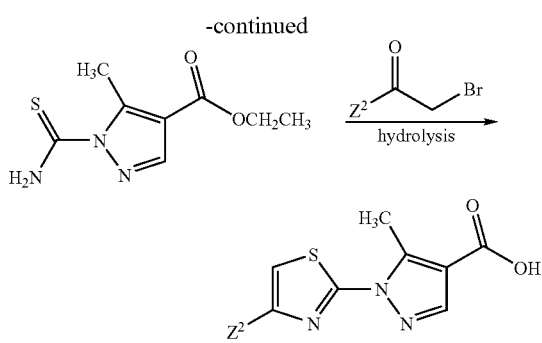

Analysis of the Compounds

A variety of in vitro and in vivo assays can be used to determine functional, chemical, and physical effects of the compounds of the present invention. Screening assays may be used to identify compounds that (1) modulate the expression and/or activity of UCP3 and (2) can be used as therapeutic agents, e.g., UCP3 upregulators or activators. The compounds can be evaluated for modulation of UCP3 expression by measuring mRNA levels by, e.g., Northern analysis, QPCR, ribonuclease protection analysis, etc. The compounds of the present invention can also be evaluated for modulation of UCP3 expression by measuring protein levels by, e.g., Western analysis, immunoprecipitation and ELISA. The compounds can be evaluated for modulation of UCP3 activity by measuring mitochondrial activity, e.g., measuring changes in the mitochondrial membrane potential.

Table 1 provides QPCR data (ABI 7700 Sequence Detection System) for exemplary compounds of formula I evaluated for UCP3 RNA induction in L6 cells from rats. The assay is described in Example 14.4, below.

TABLE 1

UCP3 RNA induction in rat L6 cells.

| Compound | Induction at 10 μM |
|---|---|
| 1 | ++ |
| 2 | ++ |
| 3 | ++ |
| 4 | ++ |
| 5 | ++ |
| 6 | ++ |
| 7 | ++ |
| 8 | — |
| 9 | — |
| 10 | + |
| 11 | + |
| 12 | — |
| 13 | + |
| 20 | + |

++ denotes greater than 10-fold induction
+ denotes 10-fold or less induction
— denotes no induction UCP3 protein was induced 2- to 3-fold in vivo (skeletal muscle tissue from Sprague-Dawley rats) after oral dosing with compound 1 (Western blot).

Table 2 provides QPCR data (ABI 7700 Sequence Detection System) for exemplary compounds of formula I evaluated for RXR induction in HEK 293 cells, following a general protocol, briefly described below. See Naeger et al. (1999) *J. Biol. Chem.* 274:1875-1878 for a related cell-based assay.

DNA constructs containing a luciferase reporter plasmid and another plasmid which contained an activation domain (e.g., RXRα) were transiently transfected into HEK 293 cells. The cells were treated with the compounds and luciferase activity was measured using a luminometer. Fold induction was determined by comparing the luciferase activity of treated cells to the activity of untreated cells.

TABLE 2

RXRα RNA induction by in HEK 293 cells.

| Compound | at 10 μM | at 3 μM | at 1 μM |
|---|---|---|---|
| 1 | + | + | ++ |
| 3 | + | + | + |
| 9 | + | + | + |
| 14 | ++ | ++ | ++ |
| 15 | + | ++ | + |
| 10 | + | ++ | + |
| 7 | + | + | + |
| 5 | + | + | + |
| 2 | + | + | + |
| 16 | + | + | + |
| 13 | + | + | + |
| 17 | + | + | + |
| 18 | + | ++ | + |
| 19 | + | + | + |
| 8 | + | + | + |

++ denotes greater than 5-fold induction
+ denotes 5-fold or less induction
— denotes no induction Combinatorial Libraries Combinatorial libraries of compounds of the invention can be screened for pharmacological activity in in vitro or in vivo assays. Conventionally, new chemical entities with useful properties are generated by identifying a chemical compound (called a "lead compound") with some desirable property or activity, e.g., UCP3 upregulating activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Millions of chemical compounds can be synthesized through such combinatorial mixing of chemical building blocks (Gallop et. al. (1994) *J. Med. Chem.* 37(9):1233-1251).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.* 37:487-493, Houghton et. al. (1991) *Nature* 354: 84-88), peptoid libraries (PCT Publication No WO 91/19735), encoded peptide libraries (PCT Publication WO 93/20242), random bio-oligomer libraries (PCT Publication WO 92/00091), benzodiazepine libraries (U.S. Pat. No. 5,288,514), libraries of diversomers, such as hydantoins, benzodiazepines and dipeptides (Hobbs et. al. (1993) *Proc. Nat. Acad. Sci. USA* 90:6909-6913), vinylogous polypeptide libraries (Hagihara et al. (1992) *J. Amer. Chem. Soc.* 114:6568), libraries of nonpeptidyl peptidomimetics with a Beta-D-Glucose scaffolding (Hirschmann et al. (1992) *J. Amer. Chem. Soc.* 114:9217-9218), analogous organic syntheses of small compound libraries (Chen et. al. (1994) *J. Am. Chem. Soc.* 116:2661), oligocarbamate libraries (Cho et al. (1993) *Science* 261:1303) and/or peptidyl phosphonate libraries (Campbell et al. (1994) *J. Org. Chem.* 59:658). See, generally, Gordon et al. (1994) *J. Med. Chem.* 37:1385-1401, nucleic acid libraries (see, e.g., Stratagene Corp.), peptide nucleic acid libraries (see, e.g., U.S. Pat. No. 5,539,083), antibody libraries (see, e.g., Vaughn et. al. (1996) *Nature Biotechnology* 14(3):309-314), and PCT/US96/10287), carbohydrate libraries (see, e.g., Liang et al. (1996) *Science* 274:1520-1522, and U.S. Pat. No. 5,593, 853), and small organic molecule libraries (see, e.g., benzodiazepines, Baum (1993) *C&EN* January 18, page 33; isoprenoids, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514; and the like).

Devices for the preparation of combinatorial libraries are commercially available (see, e.g., 357 MPS, 390 MPS, Advanced Chem Tech, Louisville Ky.; Symphony, Rainin, Woburn Mass.; 433A Applied Biosystems, Foster City Calif.; 9050 Plus, Millipore, Bedford, Mass.).

A number of well known robotic systems have also been developed for solution phase chemistries. These systems includes automated workstations like the automated synthesis apparatus developed by Takeda Chemical Industries, LTD. (Osaka, Japan) and many robotic systems utilizing robotic arms (Zymate II, Zymark Corporation, Hopkinton Mass.; Orca, Hewlett-Packard, Palo Alto Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see e.g., ComGenex, Princeton N.J.; Asinex, Moscow, Russia; Tripos, Inc., St. Louis Mo.; ChemStar, Ltd, Moscow, Russia; 3D Pharmaceuticals, Exton Pa.; Martek Biosciences, Columbia Md.; etc.).

High Throughput Screening

High throughput assays for the presence, absence, quantification, or other properties of particular compounds may be used to test a combinatorial library that contains a large number of potential therapeutic compounds (potential modulator compounds). The assays are typically designed to screen large chemical libraries by automating the assay steps and providing compounds from any convenient source to assays, which are typically run in parallel (e.g., in microtiter formats on microtiter plates in robotic assays). Preferred assays detect enhancement or upregulation of UCP3 gene transcription.

High throughput screening systems are commercially available (see e.g., Zymark Corp., Hopkinton Mass.; Air Technical Industries, Mentor Ohio; Beckman Instruments, Inc., Fullerton Calif.; Precision Systems, Inc., Natick Mass.; etc.). These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

The following examples are offered by way of illustration and not by way of limitation.

EXAMPLES

Reagents and solvents used below can be obtained from commercial sources such as Aldrich Chemical Co. (Milwaukee Wis., USA), Fisher Scientific (Loughborough UK), Acros (Loughborough UK) and ROMIL (Cambridge UK).

Method A Preparation of
Thiazol-2-yl-5-Methylpyrazol-4-Carboxylic Acids

Preparation of Hydroxymethylene Esters

Crude ethyl 2-(ethoxymethylene)-3-oxobutanoate (244 g) was stirred while adding 1.5 L of saturated aqueous copper (II) acetate over one hour. Stirring was continued for three h and the blue solid was collected, washed well with water then diethyl ether and dried to constant weight at room temperature to yield 197 g.

The solid was added to 1.4 L of ether and stirred while adding dropwise over two h 750 mL 1M sulphuric acid. The ether layer was dried (sodium sulphate), evaporated and distilled from a water bath at 75° C. using an oil pump giving product as colorless oil, b.p. 38° C./0.3 mb. Yield 135 g pure material shown by NMR to be a 9:1 mixture of geometric isomers.

Preparation of 5-Methylpyrazol-1-ylthioamides

Thiosemicarbazide (18.2 g) was stirred with 300 mL ethanol under nitrogen below −10° C. while adding dropwise 31.6 g ester (1). The mixture was stirred overnight at room temperature giving a colorless suspension.

The solid was collected, washed with ethanol and dried in air, then at 20 mb at room temperature, to a constant weight of 40.9 g. Material was stored at 4° C.

Preparation of Alkyl
Thiazol-2-yl-5-methylpyrazol-4-carboxylates 3-(Trifluoromethyl)acetophenone (7.73 g) in 50 mL dry diethyl ether was stirred while adding rapidly 2.32 mL bromine. The ether boiled gently and was stirred for 2 h after the reaction had subsided. Stirring with 50 mL water and adding sodium hydrogen carbonate in small portions until no further effervescence gave a colorless solution of ethyl 1-[4-(3-(trifluoromethyl)phenyl)thiazol-2-yl]-5-methylpyrazole-4-carboxylate (11), which was washed with brine, dried (sodium sulphate) and used directly.

Preparation of Thiazol-2-yl-5-Methylpyrazol-4-carboxylic Acids

Ester 11 (8.72 g) in 200 mL ethanol was treated with a solution of 2.2 g potassium hydroxide in 6 mL water and heated briefly when all went into solution. The potassium salt of the product separated rapidly. Water (200 mL) was added, the ethanol removed by distillation and the solution allowed to cool. Acidification with 3.9 mL concentrated hydrochloric acid and boiling briefly gave solid which was collected, washed with water and dried well in air.

The solid was dissolved in 200 mL toluene/50 nL acetone by heating and the acetone was then removed by distillation. On cooling the solid was collected, washed with toluene and dried in air, then at 110° C./20 mb, to give a constant weight of 7.56 g of 1-[4-(3-(trifluoromethyl)phenyl)thiazol-2-yl]-5-methylpyrazole-4-carboxylic acid (1).

Method B Preparation of Thiazol-2-ylpyrazole-4-carboxylic acids

Preparation of Pyrazol-1-ylthioamides

Ethyl 3,3-diethoxypropionate (Acros, 49.7 g) in 100 mL dry diethyl ether was added to a stirred suspension of 13.5 g 60% sodium hydride dispersion in oil in 300 mL ether/200 mL ethyl formate (both previously dried over 4 Å molecular sieves overnight) dropwise with ice/water cooling over 2 h. After 7 h the mixture was stirred at room temperature overnight. Hydrogen was still being evolved so the mixture was stirred for a further 48 h. Addition to water (200 mL) and washing with ether to remove starting ester gave a solution which was carefully brought to pH 3 using 3M-hydrochloric acid. Extraction with dichloromethane (3×200 mL), drying (sodium sulphate) and evaporating gave crude ethoxycarbonylmalondialdehyde as a pale orange oil which was used directly.

The above oil (15 g) in 50 mL ethanol was added at −10° C. to a suspension of 9.1 g finely powdered thiosemicarbazide in 150 mL ethanol. After stirring at room temperature for three days the solid was collected, washed with ethanol and dried in air giving an orange powder. The NMR spectrum was complex as usual for thioamides, but HPLC-MS gave a single peak having the correct mass.

Preparation of Alkyl Thiazol-2-ylpyrazole-4-carboxylates

Ethyl 3,3-diethoxypropionate (Acros, 49.7 g) in 100 mL dry diethyl ether was added to a stirred suspension of 13.5 g 60% sodium hydride dispersion in oil in 300 mL ether/200 mL ethyl formate (both previously dried over 4 Å molecular sieves overnight) dropwise with ice/water cooling over 2 h. After 7 h the mixture was stirred at room temperature overnight. Hydrogen was still being evolved so the mixture was stirred for a further 48 h. Addition to water (200 mL) and washing with ether to remove starting ester gave a solution which was carefully brought to pH 3 using 3M-hydrochloric acid. Extraction with dichloromethane (3×200 mL), drying (sodium sulphate) and evaporating gave crude ethoxycarbonylmalondialdehyde as a pale orange oil which was used directly.

The above oil (15 g) in 50 mL ethanol was added at −10° C. to a suspension of 9.1 g finely powdered thiosemicarbazide in 150 mL ethanol. After stirring at room temperature for three days the solid was collected, washed with ethanol and dried in air giving an orange powder. The NMR spectrum was complex as usual for thioamides but HPLC-MS gave a single peak having the correct mass.

3-Trifluoromethylphenacyl bromide was prepared as in Method A from 5.15 g of the acetophenone and the ether solution added to a suspension of 5.45 g of thioamide prepared as above in 200 mL ethanol/5 mL pyridine and heated under reflux in a nitrogen atmosphere overnight.

The deep brown mixture was filtered and the solid discarded. The filtrate was evaporated and the residue treated with ethanol giving 1.1 g deep yellow-brown solid with the correct NMR spectrum. Dissolving in 50 mL dichloromethane, treating with charcoal, filtering, adding 30 mL ethanol and evaporating the dichloromethane gave, on cooling, pale red-brown leaflets (0.77 g) of ethyl 1-[4-(3-(trifluoromethyl)phenyl)thiazol-2-yl]pyrazole-4-carboxylate. m.p. 158.7-159.1° C.

Preparation of Thiazol-2-ylpyrazole-4-carboxylic acids

The above ester (0.55 g) in 30 mL ethanol was treated with a solution of 0.5 g potassium hydroxide in 2 mL water and heated under reflux for two h. The ethanol was evaporated, the residue dissolved in 30 mL water, filtered and the pale yellow filtrate acidified with hydrochloric acid. The white solid was collected, washed well with water, dried briefly in air and taken up in 20 mL acetone. Addition of 40 mL toluene and heating to remove acetone and water resulted on cooling in nearly colorless solid. This was collected, washed with toluene and dried in air to a constant weight of 0.38 g of 1-[4-(3-(trifluoromethyl)phenyl)thiazol-2-yl]pyrazole-4-carboxylic acid (6).

Method C Preparation of Thiazol-2-ylpyrazole-4-carboxylic acids

Preparation of 5-(Trifluoromethyl)pyrazol-1-ylthioamides

Ethyl 2-(ethoxymethylene)-3-oxo-4,4,4-trifluorobutyrate (10.5 g) was added below −10° C. to a stirred suspension of thiosemicarbazide (3.98 g) in 60 mL ethanol and stirred overnight.

The resulting solid was collected, washed twice with ethanol and dried at 30° C./20 mb to constant weight. The product was stored at 4° C.

Preparation of Alkyl Thiazol-2-yl-5-(trifluoromethyl)pyrazole-4-carboxylates 3,5-Bis(trifluoromethyl)acetophenone (2.42 g) was converted into the phenacyl bromide in 15 mL ether using 0.50 mL bromine as in Method A. The purified ether solution was added to a stirred suspension of thioamide prepared as above (2.5 g) in 50 mL ethanol and 1.0 mL pyridine and heated under reflux after allowing the ether to escape for 3 h.

The yellow-brown solution was evaporated under vacuum, the residue treated with water then extracted into ether. Pyridine was removed by washing with saturated copper (II) acetate solution twice then with 0.5M hydrochloric acid twice. Drying (sodium sulphate) and evaporating gave 4.3 g deep brown semi-solid which was dissolved in 100 mL hot cyclohexane and treated with charcoal.

Flash chromatography (silica) using cyclohexane removed non-polar impurities and product-containing fractions were eluted with 20% ether/80% 40-60 petrol. Evaporation gave 1.65 g brown crystalline solid containing 90% product as shown by NMR. Trituration of the solid with ethanol gave pale yellow solid which was washed and dried in air to a constant weight of 1.0 g. m.p. 126.0-126.4° C.

Preparation of Thiazol-2-yl-5-(trifluoromethyl)pyrazole-4-carboxylic Acids

Ethyl 1-[4-(3,5-(bistrifluoromethyl)phenyl)thiazol-2-yl]-5-trifluoromethyl)pyrazole-4-carboxylate (0.8 g) was hydrolysed using 0.3 g potassium hydroxide/1 mL water in 15 mL ethanol as described in Method B, giving 0.37 g of 1-[4-(3,5-(bistrifluoromethyl)phenyl)thiazol-2-yl]-5-trifluoromethyl)pyrazole-4-carboxylic acid (13) as a cream crystalline solid.

Example 1

1-[4-(3-(Trifluoromethyl)phenyl)thiazol-2-yl]-5-methylpyrazole-4-carboxylic acid (1) was prepared according to Method A. m.p. 226.7-227.5° C.

Example 2

1-[4-(4-(Trifluoromethyl)phenyl)thiazol-2-yl]-5-methylpyrazole-4-carboxylic acid (2) was prepared according to Method A. m.p. 273.0-274.0° C.

Example 3

1-[4-(3,4-Dichlorophenyl)thiazol-2-yl]-5-methylpyrazole-4-carboxylic acid (3) was prepared according to Method A. m.p. 278.0-278.6° C.

Example 4

1-[4-(3-Chlorophenyl)thiazol-2-yl]-5-methylpyrazole-4-carboxylic acid (4) was prepared according to Method A. m.p. 258.0-258.3° C.

Example 5

1-[4-(3-(Trifluoromethyl)phenyl)thiazol-2-yl]-5-trifluoromethylpyrazole-4-carboxylic acid (5) was used as purchased.

Example 6

1-[4-(3-(Trifluoromethyl)phenyl)thiazol-2-yl]pyrazole-4-carboxylic acid (6) was prepared according to Method B. m.p. 229.1-229.6° C.

Example 7

1-[4-(2-(Trifluoromethyl)phenyl)thiazol-2-yl]-5-methylpyrazole-4-carboxylic acid (7) was prepared according to Method A. m.p. 215.5-216.5° C.

Example 8

Ethyl 1-[4-(3-nitrophenyl)thiazol-2-yl]-5-methylpyrazole-4-carboxylate (8) was prepared according to Method A.

Example 9

1-[4-(2-Naphthyl)thiazol-2-yl]-5-methylpyrazole-4-carboxylic acid (9) was prepared according to Method A. m.p. 273.1-274.3° C.

Example 10

1-[4-(3,5-Bis(trifluoromethyl)phenyl)thiazol-2-yl]-5-methylpyrazole-4-carboxylic acid (10) was prepared according to Method A. m.p. 260.9-261.4° C.

Example 11

Ethyl 1-[4-(3-(trifluoromethyl)phenyl)thiazol-2-yl]-5-methylpyrazole-4-carboxylate (11) was prepared according to Method A. m.p. 138-138.5° C.

Example 12

1-[4-(3-Nitrophenyl)thiazol-2-yl]-5-trifluoromethylpyrazole-4-carboxylic acid (12) was used as purchased.

Example 13

1-[4-(3,5-Bis(trifluoromethyl)phenyl)thiazol-2-yl]-5-(trifluoromethyl)pyrazole-4-carboxylic acid (13) was prepared according to Method C. m.p. 204.0-204.7° C.

Example 14

In Vitro Evaluation of Compounds of the Invention

Example 14.1

Mitochondrial Protein Preparation from Skeletal Muscle

1. Isolate rat or mouse skeletal muscle and snap freeze in liquid nitrogen. Grind into a fine powder using mortar and pestle and transfer to an eppendorf tube.

2. Resuspend skeletal muscle in Buffer 1 (0.15 mM $MgCl_2$, 10 mM KCl, 10 mM Tris-HCl, pH 6.7, stored at 4° C.).

3. Place resuspended cells on ice for 2 min. Homogenize using either Potter-Eleuhjem Teflon homogenizer and glass dounce or using hand held homogenizer for 2 min.

4. Add sucrose (1 M) to a final concentration of 0.25 M and spin at 1500 g (4000 rpm in microfuge) for 3 min. to remove nuclei.

5. Take the supernatant fraction and pellet the mitochondria by centrifugation at 10000 rpm for 10 min.

6. Resuspend pellet in 500 µl Buffer 2 (0.15 mM $MgCl_2$, 0.25 mM Sucrose, 10 mM Tris-HCl, pH 6.7, stored at 2-4° C.).

7. Spin at 10,000 rpm for 10 min.

8. Repeat steps 6 and 7.

9. Resuspend final mitochondrial pellet in 27 µl Buffer 3 (0.25 M Sucrose, 10 mM Tris-acetate, pH 7.0, 3 µl 10× protease inhibitor cocktail (BMB), stored at 4° C.).

10. Determine protein concentration with BioRad protein assay dye (Bradford Reagent). 1 µl protein in 100 µl 1× Bradford Reagent. OD595 with BSA standard curve (1 µg/µl-50 µg/µl).

11. Store at −80° C.

For antiUCP3 Westerns use 60 µg protein. Run precast 10% gels until dye front is about 1 cm from bottom of gel. Western with anti-UCP3 antibody from Alpha Diagnostics.

Example 14.2 mUCP3 QPCR Protocol

1. Plate 125,000 C2C12 cells per well (24 well plate) in 20% FBS/DMEM. Incubate for 2 days.
2. Add compounds in 20% FBS/DMEM to final concentration of 10 µM. Incubate for 18 h. 3 wells per compound.
3. Prepare RNA from cells:

Aspirate media and lyse cells directly on plate by adding 500 µL of Trizol Reagent to each well and passing the lysate several times through a pipette. Transfer lysate to eppendorf tubes (combining the lysate from identical compound treatments). Add 200 mL of chloroform to the 1 mL of lysate. Vortex to mix and incubate at room temp. for 2-3 min. Spin samples in a microfuge at 12,000 rpm for 15 min. at 4° C. Transfer the aqueous phase to a fresh tube. Precipitate the RNA from the aqueous phase by adding 500 µL of isopropanol and mixing well. Incubate at −20° C. for at least 15 min. Pellet the RNA by spinning at 12,000 rpm for 10 min. at 4° C. Remove the supernate and wash the RNA pellet with 1 mL of 75% ethanol. Spin at 12,000 rpm for 10 min. at 4° C. Remove the supernate and allow pellet to air dry briefly. Dissolve RNA in 15 µL of RNase-free water. Store at −80° C.

4. Reverse Transcription Reaction Mixture (50 µL reactions in 96 well PCR plates): TaqMan Reverse Transcription Reagents (PE catalog #N808-0234):

| Component | Volume/Tube (µL) | Final Concentration |
|---|---|---|
| RNase-free water | 15 | 1 |
| 10X TaqMan RT Buffer | 5 | 1X |
| 25 mM MgCl$_2$ | 11 | 5 Mm |
| deoxyNTPs mixture | 10 | 500 µM of each |
| Random Hexamer | 2.5 | 2.5 µM |
| RNase Inhibitor | 1.0 | 0.4 U/µL |
| MultiScribe RT | 1.25 | 1.25 U/µL |
| RNA | 5 | 50 µL |

RT Cycling Parameters
25° C. 10 min
48° C. 30 min
95° C. 5 min

5. QPCR (50 µL reactions in 96 well MicroAmp Optical Plate): TaqMan PCR Core Reagents Kit (PE catalog #N808-0228): OD cDNA and dilute to 5 ng/µL. All samples run in duplicate with mUCP3 and m18S or GAPDH probe/primers.

| Component | Volume/Tube (µL) | Final Concentration |
|---|---|---|
| RNase-free water | 19.3 | — |
| 10X TaqMan Buffer A | 5 | 1X |
| 25 mM MgCl$_2$ | 10 | 5 mM |
| 10 mM dATP | 1 | 200 µM |
| 10 mM dCTP | 1 | 200 µM |
| 10 mM dGTP | 1 | 200 µM |
| 20 mM dUTP | 1 | 400 µM |
| 10 µM Forward Primer | 0.3/0.15 | 60 nM/30 nM |
| 10 µM Reverse Primer | 0.3/0.15 | 60 nM/30 nM |
| 10 uM Probe | 0.3/0.15 | 60 nM/30 nM |
| AmpErase UNG | 0.5 | 0.01 U/µL |
| AmpliTaq Gold DNA Poly. | 0.25 | 0.025 U/µL |

Add 40 µL of Reaction Mix to 10 µL of diluted cDNA (50 ng total) on QPCR plate

PCR Cycling Parameters

| | | |
|---|---|---|
| | 50° C. | 2 min |
| | 95° C. | 10 min |
| 40 cycles: | 95° C. | 15 sec |
| | 58° C. | 1.5 min |

QPCR Primers/Probes mUCP3:

Forward Primer:
5' TGACCTGCGCCCAGC 3'                (SEQ ID NO:1)

Reverse Primer:
5' CCCAGGCGTATCATGGCT 3'             (SEQ ID NO:2)

Probe:
5' CACGGATGTGGTGAAGGTCCGATTT 3'      (SEQ ID NO:3)

GAPDH:

Forward Primer:
5' AAAGTGGAGATTGTTGCCAT 3'           (SEQ ID NO:4)

Reverse Primer:
5' TTGACTGTGCCGTTGAATT 3'            (SEQ ID NO:5)

Probe:
5' CATGTTCCAGTATGACTCCACTCACG 3'     (SEQ ID NO:6)

m18S:

Forward Primer:
5' CCCTGCCCTTTGTACACACC 3'           (SEQ ID NO:7)

Reverse Primer:
5' CGATCCGAGGGCCTCACTA 3'            (SEQ ID NO:8)

Probe:
5' CCCGTCGCTACTACCGATTGGATGGT 3'     (SEQ ID NO:9)

Example 14.3

Rat UCP3 (Skeletal Muscle) QPCR Protocol

1. Harvest skeletal muscle from rat, snap freeze in liquid nitrogen.
2. Grind skeletal muscle tissue in mortar and pestle until it is a fine powder.
3. Prepare RNA:
   (1) Add 5 mL of Trizol Reagent (Gibco BRL) and homogenize using Virtis Cyclone generator for 50 seconds.
   (2) Add another 5 mL Trizol reagent after homogenization.
   (3) Add 2 mL of chloroform to the 10 mL homogenate. Vortex to mix and incubate at room temp. for 2-3 min. Spin samples in a microfuge at 12,000 rpm for 15 min. at 4° C.
   (4) Transfer the aqueous phase to a fresh tube. Precipitate the RNA from the aqueous phase by adding 5 mL of isopropanol and mixing well. Incubate at −20° C. for at least 15 min. Pellet the RNA by spinning at 12,000 pm for 10 min. at 4° C.
   (5) Remove the supernatant and wash the RNA pellet with 5 mL of 75% ethanol. Spin at 10,000 rpm for 5 min. at 4° C.

(6) Remove the supernatant and allow pellet to air dry briefly. Dissolve RNA in 100 µL of RNase-free water. Store at −80° C. Electrophorese some RNA to check quality.

4. QPCR (50 µL reactions in 96 well MicroAmp Optical Plate):

TaqMan Gold RT-PCR Reagents (PE catalog #N808-0232): OD RNA and dilute to 5 ng/µL in RNase-free water. All samples run in duplicate with UCP3 and m18S probe/primers.

| Component | Volume/Tube (µL) | Final Concentration |
|---|---|---|
| RNase-free water | 18 | — |
| 10X TaqMan Buffer A | 5 | 1X |
| 25 mM MgCl$_2$ | 10 | 5 mM |
| 10 mM dATP | 1 | 200 µM |
| 10 mM dCTP | 1 | 200 µM |
| 10 mM dGTP | 1 | 200 µM |
| 20 mM dUTP | 1 | 400 µM |
| 10 uM Forward Primer | 0.3/0.15 | 60 nM/30 nM |
| 10 uM Reverse Primer | 0.3/0.15 | 60 nM/30 nM |
| 10 uM Probe | 0.3/0.15 | 60 nM/30 nM |
| MultiScribe RT | 0.25 | 0.25 U/µL |
| AmpliTaq Gold DNA Poly. | 0.25 | 0.025 U/µL |
| RNase Inhibitor | 1 | 0.4 U/µL |

Add 40 µL of Reaction Mix to 10 µL of diluted RNA (50 ng total) on QPCR plate

PCR Cycling Parameters
48° C. 30 min.
95° C. 10 min.
40 cycles: 95° C. 15 sec.
58° C. 1.5 min.

QPCR Primers/Probes

```
rUPC3:

Forward Primer:
5' GGCAGTGACCTGTGCTCAAC 3' (rU3-F)    (SEQ ID NO:10)

Reverse Primer:
5' CCCAGGCGTATCATGGCT 3' (mU3-R)      (SEQ ID NO:11)

Probe:
5' 6FAM-CACGGATGTGGTGAAGGTCCGATTT-    (SEQ ID NO:12)
TAMRA 3' (mU3-Probe)

m18S:

Forward Primer:
5' CCCTGCCCTTTGTACACACC 3'            (SEQ ID NO:13)

Reverse Primer:
5' CGATCCGAGGGCCTCACTA 3'             (SEQ ID NO:14)

Probe:
5' CCCGTCGCTACTACCGATTGGATGGT 3'      (SEQ ID NO:15)
```

Example 14.4

Rat UCP3 (L6 cells) QPCR Protocol 1. (Day1) Plate 300,000 L6 cells per well (24 well plate) in Minimum Essential Medium-Alpha Medium with 2% FBS and Antibiotic/Antimycotic Solution added. Incubate for 2 days and change to fresh medium (Day3). Incubate 1 more day.

2. (Day 4) Add compound at desired concentration. Incubate for 18-20 h. 2 wells per compound. 4-wells of DMSO controls per plate.

3. (Day 5) Prepare RNA from cells:
(1) Aspirate media and lyse cells directly on plate by adding 500 µL of Trizol Reagent (Gibco BRL) to each well and passing the lysate several times through a pipette. Transfer lysate to eppendorf tubes (combining the lysate from identical compound treatments).
(2) Add 200 µL of chloroform to the 1 mL of lysate. Vortex to mix and incubate at room temp. for 2-3 min. Spin samples in a microfuge at 12,000 rpm for 15 min. at 4° C.
(3) Transfer the aqueous phase to a fresh tube. Precipitate the RNA from the aqueous phase by adding 500 µL of isopropanol and mixing well. Incubate at −20° C. for at least 15 min. Pellet the RNA by spinning at 12,000 rpm for 10 min. at 4° C.
(4) Remove the supernatant and wash the RNA pellet with 500 µL of 75% ethanol. Spin at 10,000 rpm for 5 min. at 4° C.
(5) Remove the supernatant and allow pellet to air dry briefly. Dissolve RNA in 15 µL of RNase-free water. Store at −80° C. Electrophorese some RNA to check quality.

4. QPCR (50 µL reactions in 96 well MicroAmp Optical Plate): TaqMan Gold RT-PCR Reagents (PE catalog #N808-0232): OD RNA and dilute to 5 ng/µL in RNase-free water. All samples run in duplicate with UCP3 and m18S probe/primers

| Component | Volume/Tube (µL) | Concentration |
|---|---|---|
| RNase-free water | 18 | — |
| 10X TaqMan Buffer | 5 | 1X |
| 25 mM MgCl$_2$ | 10 | 5 mM |
| 10 mM dATP | 1 | 200 µM |
| 10 mM dCTP | 1 | 200 µM |
| 10 mM dGTP | 1 | 200 µM |
| 20 mM dUTP | 1 | 400 µM |
| 10 uM Forward Primer | 0.3/0.15 | 60 nM/30 nM |
| 10 uM Reverse Primer | 0.3/0.15 | 60 nM/30 nM |
| 10 uM Probe | 0.3/0.15 | 60 nM/30 nM |
| MtiScribe RT | 0.25 | 0.25 U/µL |
| AmpliTaq Gold DNA Poly. | 0.25 | 0.025 U/µL |
| RNase Inhibitor | 1 | 0.4 U/µL |

Add 40 µL of Reaction Mix to 10 µL of diluted RNA (50 ng total) on QPCR plate

PCR Cycling Parameters
48° C. 30 min.
95° C. 10 min.
40 cycles: 95° C. 15 sec.
58° C. 1.5 min.

QPCR Primers/Probes

```
rUPC3:

Forward Primer:
5' GGCAGTGACCTGTGCTCAAC 3' (rU3-F)    (SEQ ID NO:16)

Reverse Primer:
5' CCCAGGCGTATCATGGCT 3' (mU3-R)      (SEQ ID NO:17)

Probe:
5' 6FAM-CACGGATGTGGTGAAGGTCCGATTT-    (SEQ ID NO:18)
```

-continued

TAMRA 3' (mU3-Probe)

m18S:

Forward Primer:
5' CCCTGCCCTTTGTACACACC 3'    (SEQ ID NO:19)

Reverse Primer:
5' CGATCCGAGGGCCTCACTA 3'     (SEQ ID NO:20)

Probe:
5' CCCGTCGCTACTACCGATTGGATGGT 3'    (SEQ ID NO: 21)

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating obesity or diabetes, comprising administering to a subject in need thereof a therapeutically effective amount of a compound of formula (I):

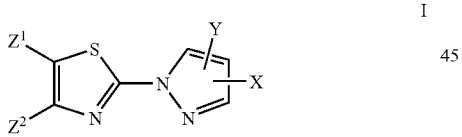

or a pharmaceutical acceptable salt or prodrug thereof, wherein

X is selected from the group consisting of $CO_2R^1$ and $C(O)NR^1R^2$;

Y is selected from the group consisting of hydrogen, $(C_1-C_4)$alkyl, fluoro$(C_1-C_4)$alkyl, aryl, heteroaryl, halogen, $NR^3R^4$ and $CO_2R^3$;

$Z^1$ is selected from the group consisting of hydrogen, $(C_1-C_4)$alkyl and halogen;

$Z^2$ is selected from the group consisting of aryl and heteroaryl, or $Z^1$ and $Z^2$ may be combined to form a fused 6-membered ring; and $R^1$, $R^2$, $R^3$ and $R^4$ are independently selected from the group consisting of hydrogen, $(C_1-C_4)$alkyl, carboxy $(C_1-C_4)$ alkyl and aryl.

2. The method of claim 1, wherein said compound has the formula (II):

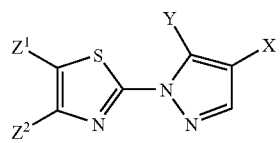

or a pharmaceutically acceptable salt or prodrug thereof, wherein

X is selected from the group consisting of $CO_2R^1$ and $C(O)NR^1R^2$;

Y is selected from the group consisting of hydrogen, $(C_1-C_4)$alkyl, fluoro$(C_1-C_4)$alkyl, aryl, heteroaryl, halogen, $NR^3R^4$ and $COR_2R^3$;

$Z^1$ is selected from the group consisting of hydrogen, $(C_1-C_4)$alkyl and halogen;

$Z^2$ is selected from the group consisting of aryl and heteroaryl, or $Z^1$ and $Z^2$ may be combined to form a fused 6-membered ring; and $R^1$, $R^2$, $R^3$ and $R^4$ are independently selected from the group consisting of hydrogen, $(C_1-C_4)$alkyl, carboxy $(C_1-C_4)$alkyl and aryl.

3. The method of claim 1, wherein X is $CO_2H$.

4. The method of claim 1, wherein Y is hydrogen. $(C_1-C_4)$ alkyl or fluoro $(C_1-C_4)$alkyl.

5. The method of claim 1, wherein $Z^1$ is hydrogen.

6. The method of claim 1, wherein $Z^2$ is phenyl, naphthyl, pyridyl or pyrimidinyl.

7. The method of claim 1, wherein $Z^2$ is phenyl and X is $CO_2H$.

8. The method of claim 1, wherein $Z^2$ is phenyl and Y is $(C_1-C_4)$alkyl or fluoro$(C_1-C_4)$alkyl.

9. The method of claim 1, wherein $Z^1$ and $Z^2$ are combined to form a fused benzene ring.

10. The method of claim 2, wherein said compound has the formula (III):

III or a pharmaceutically acceptable salt or prodrug thereof, wherein

Y is selected from the group consisting of hydrogen, $(C_1-C_4)$alkyl, fluoro$(C_1-C_4)$alkyl, aryl, heteroaryl, halogen, $NR^3R^4$ and $CO_2R^3$;

$Z^1$ is selected from the group consisting of hydrogen, $(C_1-C_4)$alkyl and halogen;

$Z^2$ is selected from the group consisting of aryl and heteroaryl, or $Z^1$ and $Z^2$ may be combined to form a fused 6-membered ring; and $R^1$, $R^3$ and $R^4$ are independently selected from the group consisting of hydrogen, $(C_1-C_4)$alkyl, carboxy $(C_1-C_4)$alkyl and aryl.

11. The method of claim 10, wherein $R^1$ is hydrogen.

12. The method of claim 10, wherein $Z^2$ is phenyl.

13. The method of claim 12, wherein said compound has the formula (IV):

IV or a pharmaceutically acceptable salt or prodrug thereof wherein

Y is selected from the group consisting of hydrogen, $(C_1-C_4)$alkyl, fluoro$(C_1-C_4$alkyl, aryl, heteroaryl, halogen, $NR^3R^4$ and $CO_2R^3$;

$R^1$, $R^2$ and $R^4$ are independently selected from the group consisting of hydrogen, $(C_1-C_4)$alkyl, carboxy $(C_1-C_4)$alkyl and aryl;

W is $(C_1-C_4)$alkyl, fluoro$(C_1-C_4)$alkyl, halogen or nitro; and n is an integer from 1 to 3.

14. The method of claim 13, wherein Y is $(C_1-C_4)$alkyl.

15. The method of claim 2, wherein said compound has the formula (VI):

VI or a pharmaceutically acceptable salt or prodrug thereof, wherein

Y is selected from the group consisting of hydrogen, $(C_1-C_4)$alkyl, fluoro$(C_1-C_4)$alkyl, aryl, heteroaryl, halogen, $NR^3R^4$ and $CO_2R^3$;

$Z^1$ is selected from the group consisting of hydrogen, $(C_1-C_4)$alkyl and halogen;

$Z^2$ is selected from the group consisting of atyl and heteroaryl, or $Z^1$ and $Z^2$ may be combined to form a fused 6-membered ring; and $R^1$, $R^2$, $R^3$ and $R^4$ are independently selected from the group consisting of hydrogen, $(C_1-C_4)$alkyl, carboxy $(C_1-C_4)$alkyl and aryl.

16. The method of claim 15, wherein $Z^2$ is phenyl.

17. The method of claim 16, wherein said compound has the formula (VII):

VII or a pharmaceutically acceptable salt or prodrug thereof, wherein

Y is selected from the group consisting of hydrogen, $(C_1-C_4)$alkyl, fluoro$(C_1-C_4)$alkyl, aryl, heteroaryl, halogen, $NR^3R^4$ and $CO_2R^3$;

$R^1$, $R^2$, $R^3$ and $R^4$ are independently selected from the group consisting of hydrogen, $(C_1-C_4)$alkyl, carboxy $(C_1-C_4)$alkyl and aryl;

W is $(C_1-C_4)$alkyl, fluoro$(C_1-C_4)$alkyl, halogen or nitro; and n is an integer from 1 to 3.

18. The method of claim 17, wherein Y is $(C_1-C_4)$alkyl.

19. The method of claim 1, wherein said compound is or

-continued

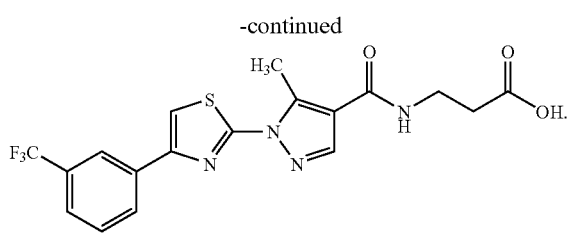

20. The method of claim 1, wherein said compound is administered in combination with a therapeutic agent selected from the group consisting of a β₃ adrenergic receptor agonist, a leptin, a lepuin derivative, a neuropeptide Y antagonist insulin and derivatives thereof, a hypoglycemic agent, an antihyperglyeemic agent, an czglucosidase inhibitor, an insulin sensitizer, an RXR agonist, a cholesterol lowering agent, a calcium channel blocker, interferon alpha, interferon beta, a DNA-alkylating agent, an antirnetabolite, a microtubule disruptor, a DNA intercalator, a DNA synthesis inhibitor and a hormone.

21. The method of claim 1, wherein said administering is oral or parenteral.

* * * * *